(12) United States Patent
Weis et al.

(10) Patent No.: US 6,384,196 B1
(45) Date of Patent: *May 7, 2002

(54) PROCESS FOR THE PREPARATION OF MINERALIZED COLLAGEN FIBRILS AND THEIR USES AS BONE SUBSTITUTE MATERIAL

(75) Inventors: Karl Weis, Freital; Wolfgang Pompe, Kurort Harta; Jens Bradt, Dresden, all of (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/275,397

(22) Filed: Mar. 24, 1999

(30) Foreign Application Priority Data

Mar. 24, 1998 (DE) .......................................... 198 12 713

(51) Int. Cl.⁷ ........................ A61K 38/17; C07K 14/00; C12P 21/06
(52) U.S. Cl. ........................ 530/356; 530/402; 514/2; 514/21; 514/801; 435/69.1
(58) Field of Search ................................. 530/356, 402; 514/2, 21, 801; 435/69.1

(56) References Cited

U.S. PATENT DOCUMENTS

| | | | | | |
|---|---|---|---|---|---|
| 5,231,169 | A | * | 7/1993 | Constantz et al. | 530/356 |
| 5,320,844 | A | * | 6/1994 | Liu | 424/422 |
| 5,405,757 | A | * | 4/1995 | Prockop et al. | 435/69.1 |
| 5,532,217 | A | * | 7/1996 | Silver et al. | 514/21 |

OTHER PUBLICATIONS

Sarto et al., *Bone*, vol. 21, No. 4, pp. 305–311, Oct. 1997.*
Lees et al., *Chemical Abstracts*, vol. 127, No. 8, p. 364, Ref-#106817C, (Calcifo. Tissue Int. vol. 61, No. 1, pp. 74–76, 1997).*

* cited by examiner

Primary Examiner—Christopher S. F. Low
Assistant Examiner—Abdel A. Mohamed
(74) Attorney, Agent, or Firm—Millen, White, Zelano & Branigan, P.C.

(57) ABSTRACT

The invention relates to a process for the preparation of mineralized collagen fibrils, where the fibril formation and mineralization take place in one process step, and to the use thereof as bone substitute material. The collagen is recombinant collagen.

11 Claims, No Drawings

PROCESS FOR THE PREPARATION OF MINERALIZED COLLAGEN FIBRILS AND THEIR USES AS BONE SUBSTITUTE MATERIAL

DESCRIPTION OF THE INVENTION

The invention relates to a process for the preparation of mineralized collagen fibrils, comprising forming the fibrils and mineralizing them in one process step. The invention farther relates to a process for the preparation of a collagen/calcium phosphate composite starting from mineralized collagen fibrils which are embedded in a calcium phosphate cement. The latter is then used as bone substitute material.

Collagenous tissue has many advantages as biomaterial compared with inorganic material. Collagen is an important protein in animals and accounts for about 30% of the proteins in vertebrates. It has the ability to assemble in vitro to fibrils, and these can be prepared in various modifications. In human bone, collagen represents, as structural material, the organic matrix in which minerals consisting of calcium, phosphate, hydroxyl, fluoride and carbonate ions, etc. are embedded. The similarity to human tissue affords an important advantage by comparison with alternative materials. This advantage is utilized for producing prostheses and biomaterials.

Numerous prior art documents dealing with the mineralization of collagen are known.

GB 1068 587 (Baxendale et al., 1963) discloses soluble collagen (from rat tails), which is reconstituted and mineralized by immersion in a supersaturated calcium phosphate solution. Assembly in the presence of ATP or chondroitin sulphate results in so-called SLS or FLS respectively, (cf. G. Reich "Kollagen", Theodor Steinkopff, Dresden (1966) p. 134 et seq.) and not, as erroneously assumed, in collagen fibrils with a 64 nm periodicity.

U.S. Pat. No. 5,320,844 (Lui, 1992) describes crosslinked collagen which is dispersed in an acidic solution and is mineralized by adding a calcium and phosphate solution with neutral pH. Either both solutions are added simultaneously, or one of the two solutions is previously mixed with the collagen.

U.S. Pat. No. 5,455,231, U.S. Pat. No. 5,231,169 and WO 93/12736 (Constantz et al.) describe a crosslinked collagen which is solubilized in basic solution, and subsequently a calcium and a phosphate solution is added dropwise over several hours. No assembly step takes place here.

U.S. Pat. No. 5,532,217 (Silver et al., 1995) discloses collagen fibres which result from an acidic collagen solution which is extruded in a neutralizing buffer. The fibres, which have a diameter of from 20 to 500 µm are subsequently mineralized, for example, in a double diffusion chamber.

The present invention has an object of providing a process for the preparation of mineralized collagen fibrils resulting in a homogeneously mineralized collagen gel. It should be used only recombinant, not natural collagen.

Another objective is to provide a process for the preparation of a collagen/calcium phosphate composite using the mineralized fibrils, and ensuring a better union between collagen and calcium phosphate cement.

It has been possible to achieve the first object in a surprisingly simple manner by a process for the preparation of mineralized collagen fibrils in which fibril formation and mineralization take place in one process step. It has been possible to achieve the second object by a process for the preparation of a collagen/calcium phosphate composite by embedding the mineralized collagen fibrils in a calcium phosphate cement in a particular ratio by weight.

The mineralized collagen fibrils are prepared from soluble collagen, which allows a higher degree of purification by comparison with the use of insoluble collagen.

The possibility of reconstituting fibrils from soluble collagen has been known for a long time (A. Veis, K. Payne, "Collagen Fibrillogenesis" from "Collagen" ed. M.E. Nimni Vol. 1, Biochemistry, CRC Boca Raton 1988).

Uncrosslinked collagen is soluble at low pH (pH $\approx$ 2) and assembles to fibrils at neutral pH. Reconstitution takes place by mixing an acidic collagen solution with a neutral buffer solution. Suitable as acidic collagen solution are all collagen solutions which comprise dissolved calcium salt (e.g., calcium chloride) at an acidic pH, preferably pH=about 2. All neutral buffer solutions are suitable as buffer solutions. Any of the types of soluble (on a molecular level) collagens routinely used for producing prosthesis and biomaterials, e.g., as cited herein, can be used in the method of the invention.

The collagen fibrils are mineralized by precipitating calcium phosphate from a supersaturated calcium phosphate solution. The supersaturation is produced by mixing a calcium component and a phosphate component. By mixing the calcium component and the phosphate component at the same time with a collagen solution and the buffer solution there is simultaneous initiation of both processes. A suitable sequence of the processes must be achieved by a suitable choice of the parameters, that is to say the fibril formation must start before the mineralization because the collagen fibrils act as template (substrate) for the mineralization. At the same time, the formation of a dense collagen structure must be restricted to such an extent that adequate diffusion of calcium and phosphate ions into the collagen fibrils is possible within a time which is worthwhile in practice. The required sequence of processes is achieved within a narrow range of parameters. The applied parameters are dependent upon one another, e.g., if a higher pH is applied, the calcium and phosphate concentrations are lower, etc. Suitable combinations can be determined with at most a few routine experiments. In general, preferred ranges of the parameters are: pH about,5–10 (after mixing both components); calcium concentration about 1 mM–50 mM; phosphate concentration about 1 mM–50 mM; and buffer concentration about 10 mM–200 mM (at least the concentration of the acid in which the collagen is dissolved). In a most preferred embodiment, calcium and phosphate solutions are in concentrations such that the solution is supersaturated with respect to hydroxyapatite (in the neutralized state), yet the concentrations are low enough so that the precipitation occurs, not immediately, but after an induction period which allows collagen fibrils to form. The resulting collagen fibrils have, in contrast to collagen fibres, a diameter of only about 20–500 nm. During the mineralization it is possible to add to the collagen fibrils according to the invention, if desired, polyaspartate, polyglutamate, polyphosphoserine, other polycarboxylates or non-collagenous proteins or phosphoproteins, or any combinations thereof, in order to improve the mineralization and influence the kinetics of the mineralization process. Bone growth factors which stimulate new bone formation can also be added, e.g., bone morphogenetic proteins (BMP), transforming growth factors (TGF), vascular growth factors (VGF), or growth and differentiation factors (GDF).

It is furthermore possible according to the invention to embed the mineralized collagen fibrils in a calcium phosphate cement in a second process step. The calcium phosphate cement is prepared from tetracalcium phosphate, calcium hydrogen phosphate, calcium hydroxyapatite, calcium dihydrogen phosphate, calcium carbonate, sodium phosphates and/or mixtures thereof, with the collagen:calcium phosphate (CaP) ratio in the resulting composite being about 1:200 to about 1:1 by weight. The individual components of the calcium phosphate cement are reduced in the solid state to a suitable particle size (e.g., 0.1 μm to 10 μm) and converted by mixing with a liquid component into a plastic composition. Curing of the cement mixtures obtained in this way takes place in two steps:

Firstly in air at room temperature for a defined period

Subsequently in an aqueous phase, which may comprise phosphate or other mineral constituents, likewise for a defined period.

The embedding of the mineralized collagen fibrils takes place by mixing them into the cement precursor. The mineralized collagen fibrils can be added in the liquid component of the cement precursor or, in the freeze-dried state, mixed with powdered components. The advantage of embedding mineralized collagen fibrils is the crosslinking with the matrix phase (calcium phosphate cement), which results in increased fracture toughness.

If required, the abovementioned non-collagenous materials can also be added during the embedding of the bone cement.

The collagen fibrils can be embedded either oriented or non-oriented, depending on the profile of requirements. This orientation can be achieved by embedding laminates of oriented fibrils. Oriented embedding makes it possible for the collagen content in the composite to be higher. It is additionally possible in this way to produce a material with anisotropic mechanical properties like those also present in bone.

Embodiments of the mineralized collagen fibrils and of the collagen/calcium phosphate composites are explained in detail in the following examples.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. DE 198 12 713.8 filed Mar. 24, 1998, is hereby incorporated by reference.

Preparation of Mineralized Collagen Fibrils:

EXAMPLE 1

Soluble collagen 1 is dissolved in a concentration of 1 mg/ml to 10 mM hydrochloric acid at a temperature of 4° C. The solution is either processed on the same day or stored deep-frozen at −80° C.

Component 1 is prepared by mixing 700 μl of collagen solution and 126μl of aqueous calcium chloride (0.1 mol/l) at 4° C.

Component 2 is prepared by mixing 165 μl of aqueous sodium chloride solution (2 mol/l), 240 μl of aqueous tris(hydroxymethyl)aminomethane solution (0.5 mol/l, pH 7.4), 32.4 μl of aqueous $KH_2PO_4/K_2HPO_4$ solution (0.5 mol/l, pH 7.4) and 793 μl of water at 4° C.

574 μl of Component 2 is added to Component 1 and mixed by shaking vigorously. After this initial mixing no further mixing is applied. Immediately after mixing the fibril formation and the mineralization is initiated by increasing the temperature rapidly from 4° to 30° C. (at least within several minutes). There is initial formation of collagen fibrils while, at the same time, an amorphous calcium phosphate phase is formed. After about 90 minutes, the amorphous calcium phosphate phase transforms by a solution/reprecipitation mechanism into crystalline defect apatite. The newly formed defect apatite deposits on the collagen fibrils, forming relatively large clusters of calcium phosphate crystals. The mixture is incubated for 24 hours at a temperature of 30° C. before further processing. The product has a gelatinous consistency. Subsequent working up takes place by centrifugation of the mineralized collagen (e.g., 10 minutes at 1000 g) and decantation of the supernatant. It is then resuspended in distilled water. This cycle is repeated several times in order to wash out buffer salts. Freeze-drying is finally carried out.

EXAMPLE 2

The collagen solution and Component 1 are as in Example 1.

Component 2 is as in Example 1, but comprises additionally 37.5 μl of aqueous sodium poly-L-aspartate solution (4 mg/ml) and 755 μl of water. The preparation takes place as in Example 1.

As in Example 1 there is initial formation of collagen fibrils and amorphous calcium phosphate. The conversion of amorphous calcium phosphate into defect apatite takes place only after about 8 hours, however. In this case, exclusively single calcium phosphate crystallites are deposited on and in the collagen fibrils. The union of calcium phosphate crystals and collagen is unambiguously improved by comparison with Example 1. The subsequent working up is analogous to Example 1.

Embedding of the Mineralized Collagen Fibrils in a Calcium Phosphate Cement

EXAMPLE 3

5 mg of mineralized collagen fibrils are added to a mixture of 500 mg of calcium dihydrogen phosphate and calcium carbonate. The mixture is stirred with 230 ml of phosphate buffer to give a plastic composition which is cured initially in air and subsequently in a phosphate buffer.

EXAMPLE 4

1 g of sodium phosphate and 288 mg of mineralized collagen fibrils are added to a mixture of 1 g of calcium dihydrogen phosphate and calcium carbonate. The mixture is stirred with water to give a plastic composition which is cured at 100% humidity.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Upon further study of the specification and appended claims, further objects and advantages of this invention will become apparent to those skilled in the art.

We claim:

1. A process for the preparation of mineralized collagen fibrils, comprising mixing an acidic solution of uncrosslinked collagen molecules, wherein the solution comprises a calcium-based mineral, with a neutral buffer solution, wherein mineralization of the fibrils begins at an acid pH, thereby forming the fibrils and mineralizing them in one step, wherein the collagen recombinant collagen.

2. The process according to claim 1, wherein the fibril formation starts before the mineralization.

3. The process according to claim 1, comprising
   a) mixing an acidic collagen solution which comprises dissolved calcium salt with a buffer solution which comprises phosphate and sodium chloride, and
   b) incubating these components at a suitable temperature, thereby forming fibrils and mineralizing them with calcium phosphate.

4. The process according to claim 1, wherein said collagen fibrils have a diameter of 20–500 nm.

5. The process according to claim 1, further comprising adding during the process step one or more of the polycarboxylates, polyaspartate, polyglutamate or polyphosphoserine, or adding one or more non-collagenous proteins or phosphoprotein, or adding a mixture thereof.

6. Mineralized collagen fibrils, prepared by the process according to claim 1.

7. A process for the preparation of a composite comprising collagen and calcium phosphate, comprising embedding mineralized collagen fibrils prepared by a process according to claim 1 in a calcium phosphate cement, wherein the ratio of collagen to calcium phosphate cement is 1:200 to 1:1 by weight.

8. The process according to claim 7, wherein the embedding of the mineralized collagen fibrils is not oriented.

9. The process according to claim 7, wherein the oriented embedding of the mineralized collagen fibrils is effected by laminates of oriented fibrils.

10. The process according to claim 7, wherein the calcium phosphate cement is prepared from tetracalcium phosphate, calcium hydrogen phosphate, calcium hydroxyapatite, calcium dihydrogen phosphate, calcium carbonate, or sodium phosphate, or mixtures thereof.

11. A method of producing bone substitute material, comprising preparing mineralized collagen fibrils by mixing an acidic solution of uncrosslinked collagen molecules, wherein the solution comprises a calcium-based mineral, with a neutral buffer solution, wherein mineralization of the fibril begins at an acid pH, thereby forming the fibrils and mineralization of them in a process step, wherein the collagen is recombinant collagen.

* * * * *

UNITED STATES PATENT AND TRADEMARK OFFICE
CERTIFICATE OF CORRECTION

PATENT NO. : 6,384,196 B1  Page 1 of 1
DATED : May 7, 2002
INVENTOR(S) : Karl Weis It is certified that error appears in the above-identified patent and that said Letters Patent is hereby corrected as shown below:

Column 5,
Line 1, reads "fibrils" should read -- fibril --
Line 4, after the word "collagen" insert -- is --
Line 21, reads "proteins" should read -- protein --

Column 6,
Line 16, reads "of" should read -- for --
Line 21, reads "mineralization of them in a" should read -- mineralizing them in one --

Signed and Sealed this

Third Day of May, 2005

JON W. DUDAS
*Director of the United States Patent and Trademark Office*